(12) United States Patent
Landingham

(10) Patent No.: US 8,268,234 B2
(45) Date of Patent: Sep. 18, 2012

(54) CERMETS FROM MOLTEN METAL INFILTRATION PROCESSING

(75) Inventor: Richard Lee Landingham, Livermore, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 0 days.

(21) Appl. No.: 13/016,459

(22) Filed: Jan. 28, 2011

(65) Prior Publication Data

US 2012/0153548 A1 Jun. 21, 2012

Related U.S. Application Data

(63) Continuation-in-part of application No. 10/260,121, filed on Sep. 27, 2002, now Pat. No. 7,879,285, and a continuation-in-part of application No. 08/829,034, filed on Mar. 31, 1997, now abandoned.

(51) Int. Cl.
*C23C 32/00* (2006.01)
*A61F 2/28* (2006.01)

(52) U.S. Cl. ...................................... 419/10; 623/23.51

(58) Field of Classification Search .................... 419/10; 623/23.51

See application file for complete search history.

(56) References Cited

U.S. PATENT DOCUMENTS

| | | | |
|---|---|---|---|
| 3,026,210 A | | 3/1962 | Cobble |
| 3,734,997 A | * | 5/1973 | Mandorf, Jr. et al. ......... 423/290 |
| 4,150,317 A | | 4/1979 | Laska et al. |
| 4,605,440 A | | 8/1986 | Halverson et al. |
| 4,718,941 A | | 1/1988 | Halverson et al. |
| 4,906,295 A | | 3/1990 | Miyamoto et al. |
| 5,041,248 A | | 8/1991 | Renlund et al. |
| 5,249,621 A | | 10/1993 | Aghajanian et al. |
| 5,296,419 A | | 3/1994 | White et al. |
| 5,308,422 A | * | 5/1994 | Askay et al. ............... 156/89.28 |
| 5,458,705 A | | 10/1995 | Mazur et al. |
| 5,511,603 A | | 4/1996 | Brown et al. |
| 5,518,974 A | | 5/1996 | Krahn et al. |
| 5,595,622 A | * | 1/1997 | Pyzik et al. ............... 156/89.28 |
| 5,624,505 A | | 4/1997 | Mazur et al. |
| 5,628,938 A | | 5/1997 | Sangeeta et al. |
| 5,676,907 A | | 10/1997 | Ritland et al. |
| 5,702,542 A | | 12/1997 | Brown et al. |
| 5,735,332 A | | 4/1998 | Ritland et al. |
| 6,025,065 A | | 2/2000 | Claussen et al. |

FOREIGN PATENT DOCUMENTS

GB 2148270 A 5/1985

OTHER PUBLICATIONS

ASM International, Materials Park, Ohio, Powder Metallurgy, vol. 7, "Mechanical Fundamentals of Consolidation", pp. 296-307.*
Halverson et al., Danny C, "Processing of Boron Carbide-Aluminum Composites" Journal of American Ceramics Society, vol. 72 No. 5, pp. 775-780. (1989).
Lide David R., ed., CRC Handbook of Chemistry and Physics Internet Version 2007 (87th Edition), <http://www.hbcpnetbase.com>.
Shell et al., Thomas E. "AC-130H Gunship Armor Upgrade Project. Part 1: Ballistic Test methods and Testing Configurations (Unclassified)" DE91, 002567, UCRL-ID-106022, Sep. 19, 1990.
Wilkins et al., Mark, "Prologue" International Journal of Applied Ceramic Technology, Ceramic Product Development and Commercialization. vol. 1 No. 3 pp. 203, 204. (2004).

* cited by examiner

*Primary Examiner* — Jessee R. Roe
(74) *Attorney, Agent, or Firm* — John P. Wooldridge

(57) ABSTRACT

New cermets with improved properties and applications are provided. These new cermets have lower density and/or higher hardness than B4C cermet. By incorporating other new ceramics into B4C powders or as a substitute for B4C, lower densities and/or higher hardness cermets result. The ceramic powders have much finer particle size than those previously used which significantly reduces grain size of the cermet microstructure and improves the cermet properties.

13 Claims, 1 Drawing Sheet

_US 8,268,234 B2_

CERMETS FROM MOLTEN METAL INFILTRATION PROCESSING

CROSS-REFERENCE TO RELATED APPLICATIONS

This application is a continuation-in-part of and claims priority to U.S. patent application Ser. No. 08/829,034 titled "Novel Cermets and Molten Metal Infiltration Method and Process for their Fabrication," filed Mar. 31, 1997, now abandoned, incorporated herein by reference. This application is a Continuation-in-part of and claims priority to U.S. patent application Ser. No. 10/260,121 titled "Process for Fabrication of Cermets," filed Sep. 27, 2002, now U.S. Pat. No. 7,879,285, incorporated herein by reference.

STATEMENT REGARDING FEDERALLY SPONSORED RESEARCH OR DEVELOPMENT

The United States Government has rights in this invention pursuant to Contract No. DE-AC52-07NA27344 between the United States Department of Energy and Lawrence Livermore National Security, LLC.

BACKGROUND OF THE INVENTION

1. Field of the Invention

The present invention relates to processing of cermet materials, and more specifically, it relates to the fabrication of cermet materials by molten metal infiltration of metals into ceramic bodies.

2. Description of Related Art

Ceramic materials have been used in advanced body armor systems to reduce weight and still defeat armor penetrating projectiles. Such projectiles can be defeated if the point of the projectiles can be blunted by the armor when a harder material (like ceramics and/or cermets) is used at the impact point. Body armor has required one of the lightest weight ceramic, boron carbide, with a fiber polymer composite backing to meet past requirements for the best body armor. New threats and the need for lighter loads for solders to carry into battle have driven new requirements for improved materials in body armor and vehicle armor. Current ceramic and cermet armors can not achieve this new requirement.

SUMMARY OF THE INVENTION

It is an object of the present invention to provide cermet materials that are processed by molten metal infiltration of ceramics.

It is another object of the present invention to provide cermet materials that have properties that are useful in armor applications.

Still another object is to provide a process that is cost effective to form molten metal infiltrated cermets with properties useful in applications like armor, cutting tools, wear parts, etc.

These and other objects will be apparent based on the disclosure herein.

Prior to the parent application, lightweight cermets fabricated by the molten metal infiltration process were limited to boron carbide (B4C) infiltrated with aluminum alloy. See U.S. Pat. No. 4,718,941. The present invention utilizes developments in the areas of lightweight ceramics, lightweight alloys, and finer starting ceramic powders to provide new cermets with improved properties and applications. These new cermets have lower density and/or higher hardness than the B4C cermet. By incorporating other new ceramics into the B4C powders or as a substitute for the B4C, lower densities and/or higher hardness are achieved in these new cermets. The ceramic powders have much finer particle size (nano-powders, 40 μm to 900 μm) than those previously used (B4C powders) which significantly reduces grain size of the cermet microstructure and improves the cermet properties over that of prior cermets (B4C—Al). These improved cermets also use lower density alloys to improve these properties and to reduce the overall cermet density.

The B4C—Al cermet was developed for opaque armor applications, both military and civilian. The present cermets can replace the B4C—Al cermets in these applications and, due to the improved properties, could find new applications in industry and in the military complex. The new applications include electrical switches, medicial instruments, wear parts and cutting tools.

BRIEF DESCRIPTION OF THE DRAWINGS

The accompanying drawings, which are incorporated into and form a part of the disclosure, illustrate embodiments of the invention and, together with the description, serve to explain the principles of the invention.

DETAILED DESCRIPTION OF THE INVENTION

Figure 1A:
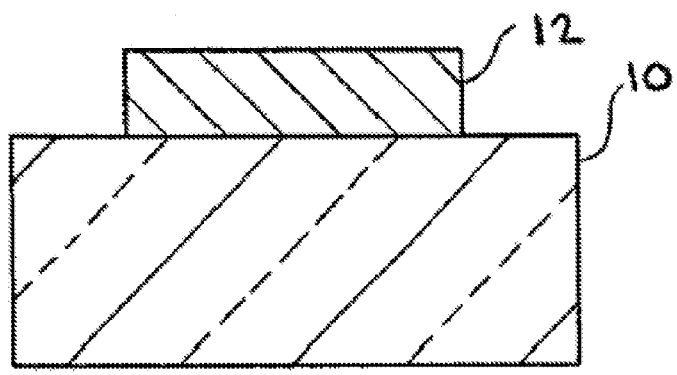
FIG. 1A shows a metal alloy on a ceramic sponge prior to metal infiltration.
Figure 1B:
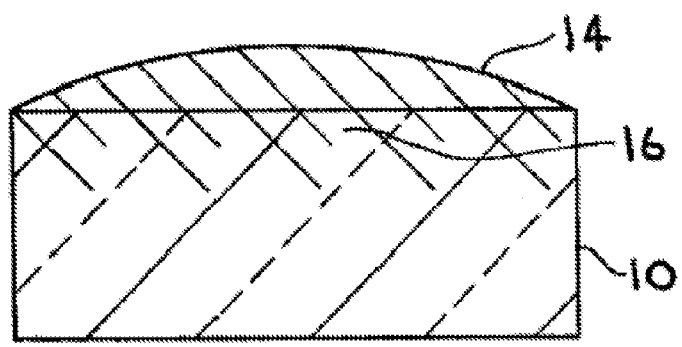
FIG. 1B shows the molten alloy infiltrating the ceramic sponge.
Figure 1C:
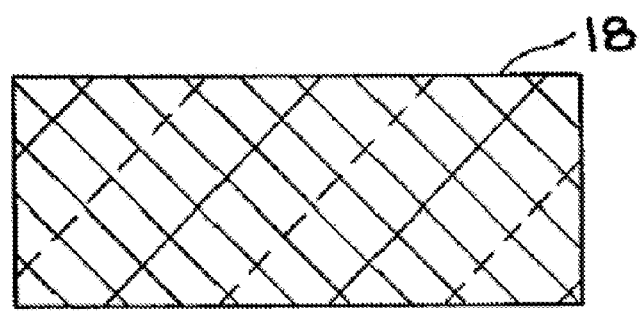
FIG. 1C shows an infiltrated cermet body after complete infiltration of molten alloy into the ceramic sponge.

Recent development of a wide variety of nano-powders has resulted in the improvement of many products and development of other products for new applications. Similar improvements are gained by applying this nano-powder technology to cermets. This is especially beneficial in the molten metal processing of cermets since lower temperatures and shorter times at temperature allow consolidation of the present cermets. These processing advantages prevent coarsing of the microstructure during processing and provide a finer grain structure in the cermets, which increases performance over previous cermets. This finer microstructure is enhanced further by the additions of lighter weight and/or harder ceramic powders in the nano-powder state.

The partial or complete substitution of boron carbide powder with these ceramic nano-powders before molten metal infiltration gives lighter weight and/or harder cermets, which results in a direct improvement in ballistic performance for armor applications. These new ceramic additions include borides, nitrides, and/or carbides of the lighter elements, e.g., Al, B, C, Mg, Be, Ca, Si, Li, Ti and V. These new ceramic substitutions also allow the additional options of using lighter weight alloys that wet the compacted ceramic bodies used in the molten metal infiltration process. A wider variety of alloys can now be used for molten metal infiltration due to improved wetting between these blended ceramics and the molten alloys. These alloys include, but are not limited to, combinations of the light elements of Al, Mg, Be, Li, Ti, V, etc. The general properties of desired alloys usable in the present invention are low density alloys (less than 2.8 gm/cc) that wet the ceramics at a reasonable temperature (<1150 C) during a relatively short infiltration period (<3 hours).

The new ceramic powders can be formed from the elements or from the pre-reacted compounds of borides, nitrides and/or carbides. Blending of the compounds is preferred in most cases due the reactive nature and/or toxicity of some elements. Blends of these nano-powder ceramics can be prepared by several methods (flame spray, milling, and/or sol-gel processes). Nano-powders of B4C can be mixed with various amounts of other nano-powders to make up the final powder blend needed to form the powder compact for molten metal infiltration. The powders should be pressed to greater than 55% of theoretical density for armor applications. Other applications may require less ceramic and more metal content for higher tensile strength and toughness but less hardness.

The metal alloys used in the molten metal infiltration process are selected for their wetability with the specific ceramic composite at a low infiltration temperature (<1150 C). The better the wetting of the molten alloy to the cermaic, the shorter the time at temperature for nearly complete infiltration (>98%). Similarly, the lower the infiltration temperature required, the shorter the time needed to complete the infiltration. Less time at the infiltration temperature results in a finer microstructure and better performance of the cermet. A typical example of forming these new cermets is the selection of the nano-powder blend of boron carbide aluminum boride and magnesium boride. This powder blend would be cold pressed to greater than 55% density and heat treated in a protective environment (vacuum, argon, etc.) to form a porous component that would have a density lower than B4C if pressed alone. A metal alloy (with good wetting characteristics for this component) would be melted in contact with the ceramic component at a low temperature in a protective atmosphere (vacuum, argon, etc.) to achieve nearly complete infiltration in a short time (<1 hour). Subsequent heat treatments of the infiltrated component could be made to adjust the properties of the cermet for a specific application. Use of the toxic element, Be, is possible if the compositions selected for the ceramic compound and/or metal alloy does not exceed toxicity limits set for this element for the specific application.

The foregoing description of the invention has been presented for purposes of illustration and description and is not intended to be exhaustive or to limit the invention to the precise form disclosed. Many modifications and variations are possible in light of the above teaching. The embodiments disclosed were meant only to explain the principles of the invention and its practical application to thereby enable others skilled in the art to best use the invention in various embodiments and with various modifications suited to the particular use contemplated. The scope of the invention is to be defined by the following claims.

We claim:

1. A method for fabricating a cermet, comprising:
providing a ceramic powder comprising nano-powder size particles;
sintering said ceramic powder at a sintering temperature to produce a porous ceramic preform matrix; and
infiltrating said matrix with a metal alloy to produce a cermet, wherein said ceramic powder comprises a blend of boron carbide, aluminum horde and magnesium boride, the method further comprising cold pressing said blend to greater than 55% density, wherein the step of sintering is carried out in a protective environment.

2. The method of claim 1, wherein said nano-powder size particles comprise a particle size within a range from about 40 nm to about 900 nm.

3. The method of claim 2, wherein said size of each particle of said particles is about the same as that of all other said particles.

4. The method of claim 1, wherein said matrix comprises a porosity within a range from about 20% to about 50%.

5. The method of claim 1, wherein the step of infiltrating said matrix comprises heating said metal alloy to at least its melting temperature.

6. The method of claim 5, wherein said melting temperature is less than said sintering temperature.

7. The method of claim 1, wherein said alloy is selected from the group consisting of Al, Mg, Be, Li, Ti and V.

8. The method of claim 1, wherein said alloy comprises a density of less than 2.8 gm cc.

9. The method of claim 8, wherein said alloy is able to wet said matrix at a temperature of less than 1150° C.

10. The method of claim 8, wherein said alloy is able to wet said matrix at a temperature of less than 1150° C. within an infiltration period of less than 3 hours.

11. The method of claim 1, wherein said metal alloy and said particle sizes are selected in combination so that said particles remain of about the same size following the step of sintering.

12. The method of claim 1, wherein the step of infiltrating infiltrates said matrix greater than 98%.

13. The method of claim 1, further comprising heat treating said cermet to adjust the properties of said cermet for a specific application.

* * * * *